United States Patent [19]

Goddard

[11] 4,003,926
[45] Jan. 18, 1977

[54] HERBICIDAL 2-ARYLAMINOCARBONYL-1-CYCLOHEXENE-1-CARBOXYLIC ACIDS AND SALTS THEREOF

[75] Inventor: Steven Jerome Goddard, West Grove, Pa.

[73] Assignee: E. I. Du Pont de Nemours and Company, Wilmington, Del.

[22] Filed: Jan. 30, 1975

[21] Appl. No.: 545,602

[52] U.S. Cl. .............................. 260/518 A; 71/115; 71/95; 260/501.15; 260/429.9; 260/429 R
[51] Int. Cl.$^2$ ........................................ C07C 63/12
[58] Field of Search ........ 260/518 A, 429.9, 429 R, 260/501.15; 71/115, 95

[56] References Cited

UNITED STATES PATENTS

| | | | |
|---|---|---|---|
| 2,556,665 | 6/1951 | Smith et al. ................ | 260/518 A |
| 2,821,467 | 1/1958 | Lewis ............................ | 260/518 A |
| 3,537,840 | 11/1970 | Barron et al. ................ | 71/115 |
| 3,654,302 | 4/1972 | Schwartz ..................... | 71/95 |
| 3,682,618 | 8/1972 | Mitchell et al. ............. | 71/115 |
| 3,878,224 | 5/1975 | Matsui et al. ................ | 71/95 |
| 3,940,419 | 2/1976 | Diehl et al. .................. | 71/95 |

OTHER PUBLICATIONS

Godt et al., J. Chem & Engin. Data, vol. 13, No. 1, pp. 137–140 (1968).
Fujinami et al., Chem Abst., vol. 65, No. 7108G (Japanese Pat. 7075(66) (1966).

Primary Examiner—Bernard Helfin
Assistant Examiner—James H. Reamer

[57] ABSTRACT

This invention relates to herbicidal 2-arylaminocarbonyl-1-cyclohexene-1-carboxylic acids and salts thereof. These compounds may be used for selective weed control in certain crops or for total vegetation control.

4 Claims, No Drawings

HERBICIDAL 2-ARYLAMINOCARBONYL-1-CYCLOHEXENE-1-CARBOXYLIC ACIDS AND SALTS THEREOF

BACKGROUND OF THE INVENTION

A number of isoindole-type compounds are known in the prior art.

Recently, in German Offenlegungsschrift No. 2,165,651 a group of isoindole-1,3-diones which are useful as herbicides was disclosed. The general formula for the isoindole-1,3-diones disclosed in the Offenlegungsschrift is as follows:

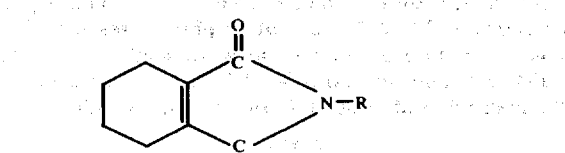

wherein R may be an aryl, aralkyl or benzyl optionally substituted with 1 to 5 halogen atoms; hydroxy, nitro, cyano, thiocyano, carboxy, halogenated alkyl, or alkyl, or alkoxy, lower alkylthio, phenyl groupings and a group having the configuration —O—CH$_2$A may also be substituted therein, wherein A is a phenyl or a naphthyl group, wherein the phenyl group may have one or more substitutions therein, such as halogen atoms, nitro groupings, lower alkyl groupings or lower alkoxy groupings.

Typical of the compounds disclosed in the Offenlegungsschrift is the compound of Example 1:

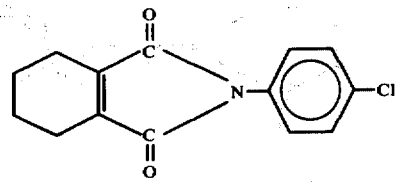

Although the compounds disclosed within the Offenlegungsschrift are active herbicides, the need still exists for herbicides which are more active still. The presence of undesired vegetation is very damaging to useful crops such as rice. In the current world situation, wherein food shortages are acute, it is more important not to lose a portion of a valuable crop such as rice. The presence of such undesired vegetation results in the loss of a significant portion of such crops. Thus, a need exists for a particularly effective herbicide which will destroy as much of this unwanted vegetation as is possible without causing significant damage to the desired crops, e.g. rice.

According to the instant invention, herbicidal compounds have been discovered which are highly active herbicides and yet cause minimal damage to certain desired crops, e.g. rice.

In U.S. Pat. No. 2,900,243, there is a disclosure of herbicidal activity for 2-(4-halophenyl)-3a,4,5,6,7,7a-hexahydro-1H-isoindole-1,3(2H)-diones; the phenyl and 2-chlorophenyl analogs are described as being inactive as herbicides.

SUMMARY OF THE INVENTION

This invention relates to the novel compounds of Formula I, to compositions containing them and to their use as herbicides

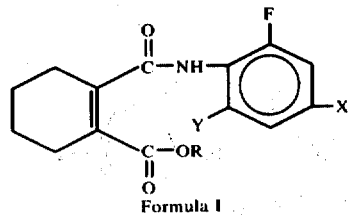

Formula I wherein
X is chlorine, bromine or fluorine;
Y is hydrogen or fluorine provided that when Y is fluorine, X is fluorine;
R is hydrogen or a cation selected from sodium, lithium, potassium, calcium, magnesium, zinc, manganese, barium or

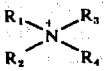

wherein
R$_1$, R$_2$, and R$_3$ can be the same or different and each can be hydrogen alkyl of 1 through 4 carbon atoms or hydroxyalkyl of 2 through 4 carbon atoms;
R$_4$ is hydrogen, alkyl of 1 through 12 carbon atoms, benzyl, or NR$_5$R$_6$ where R$_5$ is hydrogen or alkyl or 1–4 carbon atoms and R$_6$ is hydrogen or alkyl of 1 through 4 carbon atoms.

This invention also includes herbicidal compositions containing the above compounds as active ingredients and methods of controlling undesirable vegetation by applying the compounds and/or compositions to the locus of such undesired vegetation.

Preferred for their higher degree of herbicidal activity or ease of synthesis are the compounds of Formula I where
R is hydrogen, N$^+$H$_4$, HN$^+$(CH$_3$)$_3$, HN$^+$(CH$_2$CH$_2$OH)$_3$, sodium, potassium, lithium;
X is chlorine, bromine of fluorine;
Y is hydrogen or fluorine provided that when Y is fluorine, X is fluorine.

Most preferred for economic reasons and for their high herbicidal activity are the compounds of Formula I wherein:
R is hydrogen, sodium, or N$^+$H$_4$;
X is chlorine, bromine or fluorine;
Y is hydrogen or fluorine provided that when Y is fluorine, X is fluorine.

The following compounds are specifically preferred
1. 2-(4-chloro-2-fluorophenylaminocarbonyl)-1-cyclohexene-1-carboxylic acid, m.p. 91°–93° C. 2. 2-(4-chloro-2-fluorophenylcarbonyl)-1-cyclohexene-1-carboxylic acid, ammonium salt, m.p. 143°–154° C.

SYNTHESIS OF THE COMPOUNDS

The 2-arylaminocarbonyl-1-cyclohexene-1-carboxylic acids of this invention are prepared by reaction of an appropriate dihalo- or trihalo aniline with 3,4,5,6-tetrahydrophthalic anhydride as shown in the following reaction:

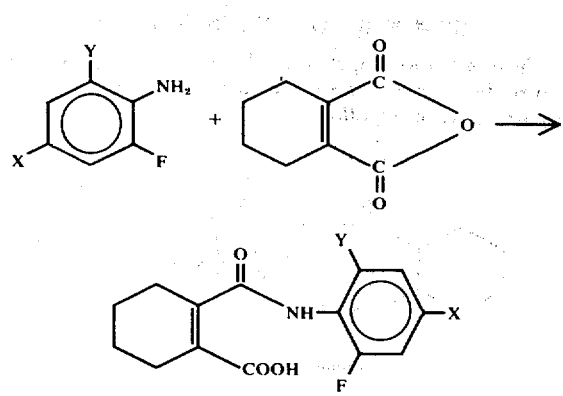

wherein

X is Cl, Br or F, and Y is H or F, provided that when Y is F, X is F.

The di- or trihaloanilines and 3,4,5,6-tetrahydrophthalic anhydride are refluxed in diethyl ether at temperatures of 35°–37° C. and atmospheric pressure for several hours, e.g. 3 to 90 hours. The 2-arylaminocarbonyl-1-cyclohexene-2-carboxylic acid is isolated by evaporation of the diethyl ether.

The quaternary ammonium salts are prepared by treating diethyl ether solution of the 2-arylaminocarbonyl-1-cyclohexene-1-carboxylic acid with an amine and filtering. The metal salts are prepared by dissolving a quaternary ammonium 2-arylaminocarbonyl-1-cyclohexene-1-carboxylate in an aqueous solution of the metal hydroxide and removing the water under reduced pressures of 20–300 mm Hg. at 25°–75° C.

Certain of the anilines employed in the synthesis of the compounds of this invention are novel. 4-Chloro-2-fluoroaniline, for example, can be prepared from 2'-fluoroacetanilide [G. Schiemann and H. G. Baumgarten, Chem. Berichte, 70, 1416 (1937)] by the sequences shown below.

STEP A

The chlorination of acetanilides in acetic acid is well known to those skilled in the art, and may be carried out under the conditions taught in W. W. Reed and K. J. P. Orton, J. Chem. Soc., 91, 1543 (1907) for the chlorination of acetanilide. The chlorination of 2'-fluoroacetanilide takes place at 25°–30° C. over several hours (e.g. 5) at atmospheric pressure. The resulting product is 4'-chloro-2'-fluoroacetanilide.

STEP B

The chlorofluoroacetanilide is refluxed in a mixture of a lower alcohol (50%) (e.g. ethanol) and concentrated hydrochloric acid (50%) for several hours (e.g. 5 or more) at 70°–90° C. and atmospheric pressure. The solvent mixture is removed at a reduced pressure of 100 to 300 mm Hg. and 20°–50° C. to leave a residue of the hydrochloride salt of 4-chloro-2-fluoroaniline.

STEP C

After basification of an aqueous solution of the hydrochloride salt of 4-chloro-2-fluoroaniline with an alkali metal hydroxide solution such as 50% sodium hydroxide at ambient conditions, the free 4-chloro-2-fluoroaniline is extracted into a suitable water-immiscible organic solvent such as ethyl ether or methylene chloride. The crude 4-chloro-2-fluoroaniline is isolated by removal of the organic solvent under reduced pressure of 100 to 300 mm Hg. at 20°–50° C.

2-Fluoro-4-bromaniline can be prepared by bromination of 2-fluoraniline [Chem. Berichte, 70, 1416 (1937)] with N-bromosuccinimide as shown in the following equation.

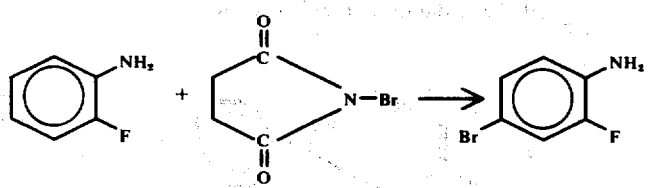

The bromination of anilines using N-bromosuccinimide in an inert organic solvent such as methylene chloride is well known to those skilled in the art, e.g., J. B. Wommack et al., J. Het. Chem, 6, 243 (1969). The bromination of 2-fluoroaniline is an exothermic reac-

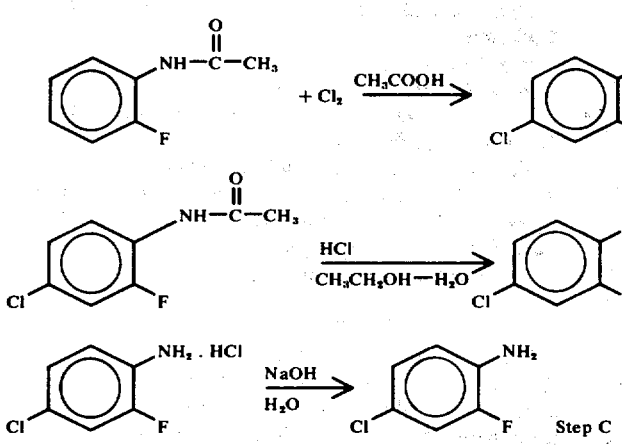

tion that takes place at 0° C. over several hours, e.g. 5 or more. The resulting reaction mixture is washed with water several times and dried with an appropriate drying agent such as anhydrous sodium sulfate. The 4-bromo-2-fluoroaniline is recovered by removal of the organic solvent under reduced pressure of 100 to 300 mm Hg. at 20°–50° C.

2,4,6-Trifluoroaniline is prepared by reduction of 1,3,5-trifluoro-2-nitrobenzene [V. I. Siele and H. J. Matsuguma, U.S. Dept. Com., Officer Serv., P B Rept., 145, 510, p. 1 (1960) or Chem. Abstr. 56, 15394c (1962)] using the procedures described by G. Schiemann and M. Seyhan, Chem. Berichte, 70, 2396 (1937).

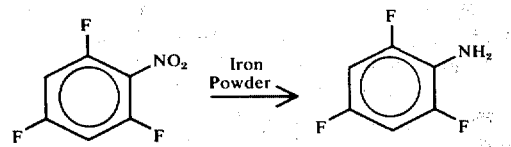

2,4-Difluoroaniline is known to the art and can be prepared by the procedure described in G. Schiemann and M. Seyhan, Chem. Berichte, 70, 2396 (1937).

The following examples further illustrate this method for synthesis of compounds of this invention. All parts are by weight and all temperatures in degrees centigrade unless otherwise indicated.

EXAMPLE 1

Preparation of 2-(4-chloro-2-fluorophenylaminocarbonyl)-1-cyclohexene-1-carboxylic acid 71 Parts of chlorine were bubbled during one hour at 25°–27° C with ice-water cooling into a solution of 140 parts of 2'-fluoroacetanilide in 500 parts of glacial acetic acid. After stirring for 4 hours at 25°–27° C, 4'-chloro-2-fluoroacetanilide precipitated. The product was collected by filtration, and the filtrate was poured into 2000 parts of ice. The resulting second portion of precipitated product was collected by filtration, combined with the first portion and recrystallized from 700 parts of methanol at −45° C to yield 119 parts of 4'-chloro-2'-fluoroacetanilide as white crystals melting at 152°–155° C.

A mixture of 119 parts of 4'-chloro-2'-fluoroacetanilide in 475 parts of ethanol and 200 parts of 37% hydrochloric acid was refluxed for 17 hours and the solvent removed under a reduced pressure of 300 mm Hg. to yield the moist, solid hydrochloride salt of 4-chloro-2-fluoroaniline.

The moist, solid hydrochloride salt of 4-chloro-2-fluoroaniline was cooled in an ice-acetone bath, down to 10° C, and 50% aqueous sodium hydroxide was added until pH 11 was reached. The resulting two-phase mixture was extracted four times; 500 parts of methylene chloride were used for each extraction. The combined organic extracts were dried with anhydrous sodium sulfate and the solvent removed under reduced pressure of 300 mm Hg. to leave 89 parts of light brown, oily 4-chloro-2-fluoroaniline, $n_D^{25}$ 1.5541.

The moist, solid hydrochloride salt of 4-chloro-2-fluoroaniline was cooled in an ice-acetone bath and treated at 10° C with 50% aqueous sodium hydroxide until pH 11 was reached. The resulting two-phase mixture was extracted four times; 500 parts of methylene chloride were used for each extraction. The combined organic extracts were dried with anhydrous sodium sulfate and the solvent removed under reduced pressure of 300 mm Hg. to leave 89 parts of light brown, oily 4-chloro-2-fluoroaniline, $n_D^{25}$ − 1.5541.

4.8 Parts of 4-chloro-2-fluoroaniline were added to a solution of 5 parts of 3,4,5,6-tetrahydrophthalic anhydride in 150 parts of diethyl ether and stirred for 1.5 hours. The solution was divided into two equal portions. One portion was evaporated under reduced pressure of 300 mm Hg. at 25° C to isolate 5.4 parts of 2-(4-chloro-2-fluorophenylaminocarbonyl)-1-cyclohexene-1-carboxylic acid as white crystals melting at 91°–93° C. The other portion was used in Example 3.

EXAMPLE 2

Preparation of 2-(2,4-difluorophenylaminocarbonyl)-1-cyclohexene-1-carboxylic acid 8.5 Parts of 2,4-difluoroaniline were added to a solution of 10 parts of 3,4,5,6-tetrahydrophthalic anhydride in 200 parts of diethyl ether and refluxed for 4 hours. The solution was evaporated under reduced pressure of 50 mm Hg. at 35° C to white crystals of 2-(2,4-difluorophenylaminocarbonyl)-1-cyclohexene-1-carboxylic acid melting at 99°–102° C.

The following 2-arylaminocarbonyl-1-cyclohexene-1-carboxylic acids can be prepared by substituting the appropriately substituted aniline for 4-chloro-2-fluoroaniline in Example 2:

2-(4-bromo-2-fluorophenylaminocarbonyl)-1-cyclohexene-1-carboxylic acid,
2-(2,4,6-trifluorophenylaminocarbonyl)-1-cyclohexene-1-carboxylic acid m.p. 105°–113° C.

EXAMPLE 3

Preparation of ammonium 2-(4-chloro-2-fluorophenylaminocarbonyl)-1-cyclohexene-1-carboxylate A slow stream of gaseous ammonia was bubbled for 15 minutes into the other portion of the diethyl ether solution of 2-(4-chloro-2-fluorophenylaminocarbonyl)-1-cyclohexene-1-carboxylic acid prepared in Example 1 until an excess of ammonia was present. A reaction proceeded at ambient temperature and pressure and the resulting product, ammonium 2-(4-chloro-2-fluorophenylaminocarbonyl)-1-cyclohexene-1-carboxylate was isolated by filtration was white crystals melting at 143°–154° C.

The 2-arylaminocarbonyl-1-cyclohexene-1-carboxylic acids of Formula I can be reacted with the following amines as 20% solutions in diethyl ether to form quaternary salts as described in Example 3.
triethanolamine
tri(4-hydroxybutyl)amine
di-n-butyl-dodecylamine
benzylamine
N,N-dimethylhydrazine
N,N-di-n-butylhydrazine

EXAMPLE 4

Preparation of trimethylammonium 2-(2,4-difluorophenylaminocarbonyl)-1-cyclohexene-1-carboxylate A slow stream of trimethylamine was bubbled into a solution of 16.8 parts of 2-(2,4-difluorophenylaminocarbonyl)-1-cyclohexene-1-carboxylic acid in 200 parts of diethyl ether for 15 minutes until an excess of trimethylamine was present. A reaction ensued at ambient temperature and pressure and the resulting precipitate was filtered to yield 14.7 parts of trimethylammonium 2-(2,4-difluorophenylaminocarbonyl)-1-cyclohexene-1-carboxylate as a white solid melting at 114°–116° C with decomposition.

Example 5

Preparation of lithium 2-(2,4-difluorophenylaminocarbonyl)-1-cyclohexene-1-carboxylate Six parts of trimethylammonium 2-(2,4-difluorophenylaminocarbonyl)-1-cyclohexene-1-carboxylate were dissolved in 10 parts of 2N lithium hydroxide solution. The solution was evaporated under reduced pressure of 20 mm Hg. at 50° C to 4.5 parts of lithium 2-(2,4-difluorophenylaminocarbonyl)-1-cyclohexene-1-carboxylate as a white solid melting 210°–225° C.

By substituting the appropriate metal hydroxide for lithium hydroxide in the procedure of Example 5, the 2-arylaminocarbonyl-1-cyclohexene-1-carboxylic acids of Formula I (R=H) can be converted to salts of Formula I having the following values of R.

R sodium
potassium
calcium (hemi-salt)
magnesium (hemi-salt)
zinc (hemi-salt)
manganese (hemi-salt)
barium (hemi-salt)

FORMULATIONS

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few pints to several hundred gallons per acre. High strength compositions are primarily used as intermediates for further formulation. The formulations, broadly, contain about 1% to 99% by weight of active ingredient(s) and at least one of a) about 0.1% to 20% surfactant(s) and b) about 5% to 99% solid or liquid diluent(s). More specifically, they will contain these ingredients in the following approximate proportions:

|  | Percent by Weight | | |
|---|---|---|---|
|  | Active Ingredient | Diluent(s) | Surfactant(s) |
| Wettable Powders | 20–90 | 0–74 | 1–10 |
| Oil Suspensions, Emulsions, Solutions (including Emulsifiable Concentrates) | 5–50 | 40–95 | 0–15 |
| Aqueous Suspensions | 10–50 | 40–84 | 1–20 |
| Dusts | 1–25 | 70–99 | 0–5 |
| Granules and Pellets | 1–95 | 5–99 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd. Edn., Dorland Books, Caldwell, N.J. The more absorptive diluents are preferred for wettable powders and the denser ones for dusts. Typical liquid diluents and solvents are described in Marsden, "Solvents Guide", 2nd. Edn., Interscience, New York, 1950. Solubility under 0.1% is preferred for suspension concentrates; solution concentrates are preferably stable against phase separation at 0° C. "McCutcheon's Detergents and Emulsifiers Annual", Allured Publ. Corp., Ridgewood New Jersey, as well as Sisely and Wood, "Encylopedia of Surface Active Agents", Chemical Publ. Co., Inc. New York, 1964, list surfactants and recommended uses. All formulations can contain minor amounts of additives to reduce foam, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 4th. Edn., McGraw-Hill, N.Y., 1963, pp. 8-59ff.

For further information regarding the art of formulation, see for example:

H. M. Loux, U.S. Pat. No. 3,235,361, Feb. 15, 1966, Col. 6, Line 16 through Col. 7, Line 19 and Examples 10 through 41.

R. W. Luckenbaugh, U.S. Pat. No. 3,309,192, Mar. 14, 1967, Col. 5 Line 43 through Col. 7 Line 62 and Ex. 8, 12, 15, 39, 41, 52, 53, 58, 132, 138–140, 162–164, 166, 167, 169–182.

H. Gysin and E. Knüsli, U.S. Pat. No. 2,891,855, June 23, 1959, Col. 3 Line 66 through Col. 5 Line 17 and Examples 1–4.

G. C. Klingman, "Weed Control as a Science", John Wiley & Sons, Inc., New York, 1961 pp. 81–96.

J. D. Fryer and S. A. Evans, "Weed Control Handbook", 5th Edn. Blackwell Scientific Publications, Oxford, 1968, pp. 101–103.

Example 6

| Wettable Powder | Percent |
|---|---|
| 2-(4-chloro-2-fluorophenylcarbamoyl)-1-cyclohexene-1-carboxylic acid, ammonium salt | 40% |
| dioctyl sodium sulfosuccinate | 1.5% |
| sodium ligninsulfonate | 3% |
| low viscosity methyl cellulose | 1.5% |
| attapulgite | 54% |

The ingredients were thoroughly blended, passed through an air mill, to produce an average particle size under 15 microns, reblended, and sifted through a U.S.S. No. 50 sieve (0.3mm opening) before packaging.

All compounds of the invention may be formulated in the same manner.

Example 7

| Aqueous Suspension | Percent |
|---|---|
| 2-(4-chloro-2-fluorophenylaminocarbonyl)-1-cyclohexene-1-carboxylic acid | 25% |
| hydrated attapulgite | 3% |
| crude calcium ligninsulfonate | 10% |
| sodium dihydrogen phosphate | 0.5% |
| water | 61.5 |

The ingredients were ground together in a ball or roller mill until the solid particles have been reduced to diameters under 10 microns.

Example 8

| Solution and Granules | Percent |
|---|---|
| 2-(4-chloro-2-fluorophenylaminocarbonyl)-1-cyclohexene-1-carboxylic acid | 25% |
| dichloromethane | 25% |

The ingredients were combined and stirred to produce a solution. This solution was then sprayed onto preformed montmorillonoid clay granules (0.6–2.5 mm in diameter) tumbling in a rotating drum. The rate of spray was adjusted to produce a 5% active granule after the dichloromethane was removed by evaporation. These granules were then packaged.

Example 9

| High Strength Concentrate | Percent |
|---|---|
| 2-(4-chloro-2-fluorophenylaminocarbonyl)-1-cyclohexene-1-carboxylic acid, ammonium salt | 98.5% |
| silica aerogel | 0.5% |
| synthetic amorphous fine silica | 1.0% |

The above listed ingredients were blended and ground in a hammer mill to produce a high strength concentrate essentially all passing a U.S.S. No. 50 sieve (0.3 mm openings). This material may then be formulated in a variety of ways known to one skilled in the art.

Example 10

| Dust | Percent |
|---|---|
| high strength concentrate, Example 9 | 25.4% |
| pyrophyllite, powdered | 74.6% |

The materials were thoroughly blended and packaged for use.

Example 11

| Oil Suspension | Percent |
|---|---|
| 2-(4-chloro-2-fluorophenylaminocarbonyl)-1-cyclohexene-1-carboxylic acid | 25% |
| polyoxyethylene sorbitol hexaoleate | 5% |
| highly aliphatic hydrocarbon oil | 70% |

The ingredients were ground together in a sand mill until the solid particles have been reduced to under about 5 microns. The resulting thick suspension may be applied directly, but preferably after being extended with oils or emulsified in water.

UTILITY

The compounds of formula I are useful for the selective preemergence weed control of undesired vegetation in crops such as rice, soybeans, peanuts, lima beans, green beans and squash. The compounds of this invention also can be used as directed treatments for the pre/post-emergence control of weeds in various crops including soybeans, peanuts, garden beans and row-planted rice. In addition, these compounds are useful wherever general weed control is required, such as industrial sites, railroad and utility rights-of-way, along fences, building foundations, parking and storage lots, etc.

The precise amount of the compounds of Formula I to be used in any given situation will vary according to the particular end result desired, the plant and soil involved, the formulation used, the mode of application, prevailing weather conditions, foliage density and like factors. Since so many variables play a role, it is not possible to state a rate of application suitable for all situations. Broadly speaking, the compounds of the invention are used at levels of about 0.125 to about 20 kilograms, preferably about 0.25 to about 10, per hectare. The lower rates in this range will generally be selected on lighter soils, soils low in organic matter content, for selective weed control in crops, or in situations where maximum persistence is not necessary.

Herbicidal activity of compounds of this invention was discovered in a greenhouse test.

TEST PROCEDURE

Seeds of crabgrass (*Digitaria spp.*), barnyard-grass (*Echinochloa crusgalli*) wild oats (*Avena fatua*). Cassia tora, morningglory (*Ipomoea spp.*), cocklebur (*Xanthum spp.*), sorghum, corn, soybean, rice, wheat and nutsedge tubers were planted in a growth medium and treated preemergence with the chemicals dissolved in a non-phytotoxic solvent. At the same time, cotton having five leaves (including cotyledonary ones), bush beans with the third trifoliate leaf expanding, crabgrass with two leaves, barnyardgrass with two leaves, wild oats with one leaf, cassia with three leaves (including cotyledonary ones), morningglory with four leaves (including the cotyledonary ones), cocklebur with four leaves (including the cotyledonary ones), sorghum with three leaves, corn with three leaves, soybean with two cotyledonary leaves, rice with two leaves, wheat with one leaf, and nutsedge with three-five leaves were sprayed. Treated plants and controls were maintained in a greenhouse for 16 days, then all species were compared to controls and visually rated for response to treatment. A quantitative rating was made on a scale of 0 to 10; a rating of 10 means complete kill, a rating of 0 means no injury. A qualitative rating for type of injury was also made; the letter "B" indicates foliage burn, "E" denotes emergence inhibition, "C" means chlorosis/necrosis and "H" stands for formative effects.

Ratings for one of the compounds tested by this procedure are recorded in Table 1.

| COMPOUND | | | | | | | | | | | | | |
|---|---|---|---|---|---|---|---|---|---|---|---|---|---|

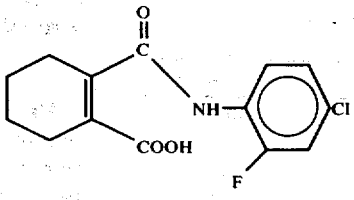

| | | | | | | | POST EMERGENCE | | | | | | |
|---|---|---|---|---|---|---|---|---|---|---|---|---|---|
| Kg. Ha. | Bush Bean | COT-TON | MORN-ING GLORY | COC-KLE-BUR | CAS-SIA | NUT-SEDGE | CRAB-GRASS | BARN-YARD GRASS | WILD OATS | WHEAT | CORN | SOY-BEAN | RICE | SOR-GHUM |
| 2 | 10B | 10B | 10B | 10B | 10B | 5B | 10B | 10B | 9B | 8B | 8B | 9B | 9B | 10B |

| | | | | PRE-EMERGENCE | | | | | | | |
|---|---|---|---|---|---|---|---|---|---|---|---|
| MORN-ING GLORY | COC-KLE-BUR | CAS-SIA | NUT-SEDGE | CRAB-GRASS | BARN-YARD GRASS | WILD OATS | WHEAT | CORN | SOY-BEAN | RICE | SOR-GHUM |
| 5H | 10E | 10C | 7C | 10E | 10C | 10C | 9C | 8C | 9G | 9 | 10C |

From the above data, it is seen that a representative compound of the instant invention is a highly effective herbicide. For instance, if applied postemergence, a compound of the instant invention destroyed many different forms of noxious vegetation such as barnyardgrass, cocklebur, and morningglory.

What is claimed is:

1. A compound of the formula

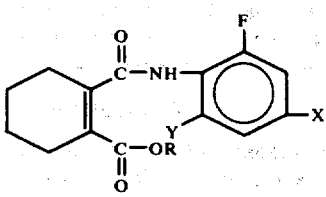

wherein

X is chlorine, bromine or fluorine;

Y is hydrogen or fluorine provided that when Y is fluorine, X is fluorine;

R is hydrogen or a cation selected from sodium, lithium, potassium, calcium, magnesium, zinc, manganese, barium or

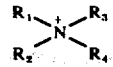

wherein $R_1$, and $R_2$, and $R_3$ can be the same or different and each can be hydrogen alkyl of 1 through 4 carbon atoms or hydroxyalkyl of 2 through 4 carbon atoms;

$R_4$ is hydrogen, alkyl of 1 through 12 carbon atoms, benzyl, or $NR_5R_6$ where $R_5$ is hydrogen or alkyl of 1–4 carbon atoms and $R_6$ is hydrogen or alkyl of 1 through 4 carbon atoms.

2. A compound of claim 1 wherein R is hydrogen, $N^+H_4$, $HN^+(CH_3)_3$, $HN^+(CH_2CH_2OH)_3$, sodium, potassium, or lithium; X is chlorine, bromine or fluorine; and Y is hydrogen or fluorine provided that when Y is fluorine, X is fluorine.

3. A compound of claim 1 wherein R is a hydrogen, sodium, or ammonium; X is chlorine, bromine, or fluorine; and Y is hydrogen or fluorine, provided that when Y is fluorine, X is fluorine.

4. A compound of claim 1, 2-(4-chloro-2-fluorophenylaminocarbonyl)-1-cyclohexene-1-carboxylic acid, ammonium salt.

* * * * *